United States Patent
Gal et al.

(10) Patent No.: US 12,182,874 B2
(45) Date of Patent: Dec. 31, 2024

(54) POPULATION HEALTH MANAGEMENT TO DEFER LONG TERM CARE IN THE SHORT TERM

(71) Applicant: Assured Inc., Wellesley, MA (US)

(72) Inventors: Afik Gal, Needham, MA (US); Roee Nahir, Ramat Hasharon (IL); Yaron David, Haifa (IL); Hila Zadka-Schuldiner, Mevasseret Tzion (IL); Yariv Dror Mizrahi, Ra'anana (IL); Yehonatan Yedidia, Tel Aviv (IL)

(73) Assignee: Assured Inc., Wellesley, MA (US)

( * ) Notice: Subject to any disclaimer, the term of this patent is extended or adjusted under 35 U.S.C. 154(b) by 0 days.

(21) Appl. No.: 17/406,131

(22) Filed: Aug. 19, 2021

(65) Prior Publication Data

US 2022/0058748 A1 Feb. 24, 2022

Related U.S. Application Data

(60) Provisional application No. 63/068,028, filed on Aug. 20, 2020.

(51) Int. Cl.
*G06Q 40/08* (2012.01)

(52) U.S. Cl.
CPC .................................. *G06Q 40/08* (2013.01)

(58) Field of Classification Search
None
See application file for complete search history.

(56) References Cited

U.S. PATENT DOCUMENTS

| 7,693,728 B2* | 4/2010 | Underwood | G06Q 40/08 705/2 |
| 10,740,437 B1* | 8/2020 | Shannon | G16H 10/60 |
| 11,056,242 B1 | 7/2021 | Jain | |
| 2001/0020229 A1* | 9/2001 | Lash | G16Z 99/00 705/3 |
| 2002/0087364 A1* | 7/2002 | Lerner | G06Q 40/08 705/4 |

(Continued)

FOREIGN PATENT DOCUMENTS

| WO | 199901836 A1 | 1/1999 |
| WO | WO-2019246032 A1 * | 12/2019 |

*Primary Examiner* — William J Jacob
(74) *Attorney, Agent, or Firm* — Heidi Brun Associates Ltd.

(57) ABSTRACT

A system for population health management to enable policy holders to defer long term care for the near term includes an external data gatherer, a model builder and an intervention determiner. The external data gatherer gathers data about a plurality of policy holders from at least two of medical records, direct observation, third party data sources, and questionnaires about lifestyles, family and caregivers. The model builder builds a model from at least one of scientifically based research and the gathered data and determines which of the policy holders are likely to claim for long term care in the near term. The intervention determiner determines, for a particular policy holder, at least one scientifically based intervention to improve a probability that the particular policy holder remain at home for another year.

10 Claims, 6 Drawing Sheets

(56) References Cited

U.S. PATENT DOCUMENTS

| | | | |
|---|---|---|---|
| 2008/0177567 A1* | 7/2008 | Friedlander | G16Z 99/00 |
| | | | 705/2 |
| 2009/0276161 A1 | 11/2009 | Cobain | |
| 2012/0226630 A1 | 9/2012 | Sawyer | |
| 2014/0089836 A1 | 3/2014 | Damani | |
| 2015/0134344 A1 | 5/2015 | Turrentine | |
| 2016/0378942 A1* | 12/2016 | Srinivas | G16H 50/30 |
| | | | 705/2 |
| 2017/0185727 A1 | 6/2017 | Harris | |
| 2017/0262604 A1* | 9/2017 | Francois | G16H 10/60 |
| 2019/0122770 A1 | 4/2019 | Pengetnze | |
| 2019/0214113 A1* | 7/2019 | Abramowitz | G06F 16/9535 |
| 2019/0371472 A1* | 12/2019 | Blanchard | G16H 10/60 |
| 2021/0118557 A1* | 4/2021 | Pauws | G06N 7/005 |

* cited by examiner

| CATEGORIES | QUESTIONS |
|---|---|
| LIVING ENVIRONMENT | ARE YOU ABLE TO TRAVEL AROUND THE LOCAL AREA/COMMUNITY WITHOUT PROBLEMS? |
| LIVING ENVIRONMENT | WALKABILITY: DEDICATED SIDEWALKS AND MARKED CROSSINGS FOR PEDESTRIANS, AND SHOPS, PARKS, AND OTHER DESTINATIONS WITHIN WALKING DISTANCE. WEATHER AND CLIMATE MATTER TOO. |
| HOME ACCESSIBILITY | ADJUSTING TOILET HEIGHT OR INSTALLING A SEAT EXTENDER |
| HOME ACCESSIBILITY | DOES THE ENTRANCE DOOR HAVE A SECURITY PEEPHOLE OR VIEW PANEL AT THE CORRECT HEIGHT FOR YOU? |
| FINANCIAL SUSTAINABILITY | ARE YOU REASONABLY CONFIDENT THAT YOUR MONTHLY MORTGAGE OR RENT PAYMENT WILL CONTINUE TO BE AFFORDABLE IF OTHER EXPENSES IN YOUR LIFE WERE TO INCREASE SUBSTANTIALLY (I.E. MEDICAL EXPENSES, SUPPORTIVE SERVICES)? |
| FINANCIAL SUSTAINABILITY | DO YOU HAVE THE FINANCIAL RESOURCES TO MAINTAIN YOUR HOME (OR PAY SOMEONE TO DO IT )? |
| MEDICAL | DO YOU VISIT YOUR MEDICAL PROVIDER AT LEAST ANNUALLY FOR A ROUTINE CHECKUP AND TESTING? |
| LIFE ENGAGEMENT | ARE YOU A MEMBER OF OR DO YOU BELONG TO ANY RELIGIOUS INSTITUTIONS, CLUBS, LOCAL GROUPS, ALUMNI ASSOCIATIONS, ETC.? |
| MENTAL | HOW OFTEN DO YOU FEEL THAT YOU LACK COMPANIONSHIP? |
| FUNCTIONALITY | HAVE YOU NOTICED THAT YOU LIMIT OR MODIFY YOUR DRIVING IN ANY OF THE FOLLOWING CIRCUMSTANCES OR SETTINGS: NIGHT, HEAVY TRAFFIC, HIGHWAY, UNFAMILIAR PLACES? |

FIG. 2

| SCORE | QUESTIONS |
|---|---|
| Y: 1  N: 0 | ARE YOU ABLE TO TRAVEL AROUND THE LOCAL AREA/COMMUNITY WITHOUT PROBLEMS? WALKABILITY: DEDICATED SIDEWALKS AND MARKED CROSSINGS FOR PEDESTRIANS, AND SHOPS, PARKS, AND OTHER DESTINATIONS WITHIN WALKING DISTANCE. WEATHER AND CLIMATE MATTER TOO. |
| Y: 1  N: 0 | DOES THE ENTRANCE DOOR HAVE A SECURITY PEEPHOLE OR VIEW PANEL AT THE CORRECT HEIGHT FOR YOU? |
| Y: 1  N: 0 | ARE YOU REASONABLY CONFIDENT THAT YOUR MONTHLY MORTGAGE OR RENT PAYMENT WILL CONTINUE TO BE AFFORDABLE IF OTHER EXPENSES IN YOUR LIFE WERE TO INCREASE SUBSTANTIALLY (I.E. MEDICAL EXPENSES, SUPPORTIVE SERVICES)? |
| Y: 1  N: 0 | DO YOU HAVE THE FINANCIAL RESOURCES TO MAINTAIN YOUR HOME (OR PAY SOMEONE TO DO IT )? |
| Y: 1  N: 0 | DO YOU VISIT YOUR MEDICAL PROVIDER AT LEAST ANNUALLY FOR A ROUTINE CHECKUP AND TESTING? |
| Y: 1  N: 0 | ARE YOU A MEMBER OF OR DO YOU BELONG TO ANY RELIGIOUS INSTITUTIONS, CLUBS, LOCAL GROUPS, ALUMNI ASSOCIATIONS, ETC. |
| >3: 1  N: 0 | HOW OFTEN DO YOU FEEL THAT YOU LACK COMPANIONSHIP? |
| Y: 1  N: 0 | HAVE YOU NOTICED THAT YOU LIMIT OR MODIFY YOUR DRIVING IN ANY OF THE FOLLOWING CIRCUMSTANCES OR SETTINGS: NIGHT, HEAVY TRAFFIC, HIGHWAY, UNFAMILIAR PLACES? |

FIG. 3

| | |
|---|---|
| CHRONIC DISEASE—INADHERANCE TO CARE PLAN (MODERATE) | EXECUTE IADL—MEDICATION ARF<br>EXECUTE MEDICATION ARF |
| IADL—NUTRITION (MODERATE) | ARRANGE HOME OPTIMIZATION SERVICES<br>ARRANGE HOME MODIFICATION<br>SET UP MEALS ON WHEELS ACCOUNT<br>SET UP ONGOING MEAL DELIVERY SERVICE<br>SET UP GROCERY DELIVERY SERVICE |
| IADL—TRANSPORTATION | SET UP MEMBER WITH LOCAL TRANSPORTATION OPTIONS<br>SET UP RIDE SHARING SERVICE<br>SET UP GOGO ACCOUNT FOR RIDE SHARE |
| SOCIAL ISOLATION/LOW LIFE ENGAGEMENT (LOW) | CREATE ACTIVITY CALENDAR<br>EDUCATE ON ONLINE ACTIVITIES/VIDEO CONFERENCING<br>CONNECT WITH FRIENDSHIP LINE/LOCAL COA/SENIOR CENTER |

FIG. 6

POPULATION HEALTH MANAGEMENT TO DEFER LONG TERM CARE IN THE SHORT TERM

CROSS REFERENCE TO RELATED APPLICATIONS

This application claims priority from U.S. provisional patent application 63/068,028, filed Aug. 20, 2020, which is incorporated herein by reference.

FIELD OF THE INVENTION

The present invention relates to insurance generally and to long term care insurance in particular.

BACKGROUND OF THE INVENTION

Long term care insurance (LTCI) is a relatively new type of insurance that covers the costs of nursing home care and/or long-term care at home. It is typically activated when policy holders become incapacitated in some way but either don't need or don't want to move out of their home in order to receive the care they need.

LTCI insurance is expensive and open-ended, as some of the policy holders will need the care for an extended period of time.

SUMMARY OF THE PRESENT INVENTION

There is therefore provided, in accordance with a preferred embodiment of the present invention, a method for population health management to enable policy holders to defer long term care for the near term. The method includes gathering data about a plurality of policy holders from at least two of: medical records, direct observation, third party data sources, and questionnaires about lifestyles, family and caregivers, building a model from at least one of scientifically-based research and the gathered data to determine which policy holders are likely to claim for long term care in the near term, and for a particular policy holder, determining at least one scientifically-based intervention to improve a probability that the particular policy holder remain at home for another year.

Moreover, in accordance with a preferred embodiment of the present invention, the gathering data includes providing scores to the data and generating features as a function of the scores.

Further, in accordance with a preferred embodiment of the present invention, the gathering data includes selecting the plurality of policy holders from among a block of policy holders according to their scores on the features.

Still further, in accordance with a preferred embodiment of the present invention, building a model includes utilizing a probability based, predictive model as a function of the scores of the plurality of policy holders on the features.

Additionally, in accordance with a preferred embodiment of the present invention, the building a model includes generating impact coefficients for each the feature of the features.

Further, in accordance with a preferred embodiment of the present invention, the probability based, predictive model is based on at least one feature which is a function of age and at least a second feature which is a function of the square of the age.

Still further, in accordance with a preferred embodiment of the present invention, the building a model includes calculating a match to the scores using the age feature and the square of the age feature, picking another feature, selecting another feature if a match to the scores has improved, and repeating the calculating, picking and selecting until there are either no more features or no more improvement to the match.

Further, in accordance with a preferred embodiment of the present invention, the determining includes utilizing the model on scores of the particular policy holder to determine a risk level of the particular policy holder. It also includes if the risk level is above a predetermined level, rerunning the model with a change in a feature, checking if the rerun model produces a reduced risk level, and if the risk level is reduced, suggesting one or more interventions related to the changed feature to the particular policy holder.

Still further, in accordance with a preferred embodiment of the present invention, the building a model including building an initial model from the scientifically based research and updating the initial model with data from the policy holders.

Additionally, in accordance with a preferred embodiment of the present invention, the policy holders are at least 80 years old.

There is also provided, in accordance with a preferred embodiment of the present invention, system for population health management to enable policy holders to defer long term care for the near term. The system includes an external data gatherer, a model builder and an intervention determiner. The external data gatherer gathers data about a plurality of policy holders from at least two of medical records, direct observation, third party data sources, and questionnaires about lifestyles, family and caregivers. The model builder builds a model from at least one of scientifically based research and the gathered data and determines which of the policy holders are likely to claim for long term care in the near term. The intervention determiner determines, for a particular policy holder, at least one scientifically based intervention to improve a probability that the particular policy holder remain at home for another year.

Further, in accordance with a preferred embodiment of the present invention, the external data gatherer provides scores to the data, generates features as a function of the scores, and also selects the plurality of policy holders from among a block of policy holders according to their scores on the features.

Still further, in accordance with a preferred embodiment of the present invention, the model builder generates a probability based, predictive model as a function of the scores of the plurality of policy holders on the features, and also generates impact coefficients for each the feature of the features.

Moreover, in accordance with a preferred embodiment of the present invention, the model builder calculates a match to the scores using the age feature and the square of the age feature, picks another feature, selects another feature if a match to the scores has improved, and repeats until there are either no more features or no more improvement to the match.

Further, in accordance with a preferred embodiment of the present invention, the intervention determiner utilizes the model on scores of the particular policy holder to determine a risk level of the particular policy holder, if the risk level is above a predetermined level, reruns the model with a change in a feature, checks if the rerun model produces a reduced risk level, and if the risk level is reduced, suggests one or more interventions related to the changed feature to the particular policy holder.

Still further, in accordance with a preferred embodiment of the present invention, the model builder builds an initial model from the scientifically based research and updating the initial model with data from the policy holders.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 2 is an illustration of an exemplary questionnaire which may be used for an assessment, useful in the method of FIG. 1;

FIG. 3 is an illustration of an exemplary method of scoring the questionnaire of FIG. 2, useful in the method of FIG. 1;

FIG. 6 is a tabular illustration of an intervention table, useful in the system of FIG. 1.

Figure 1:
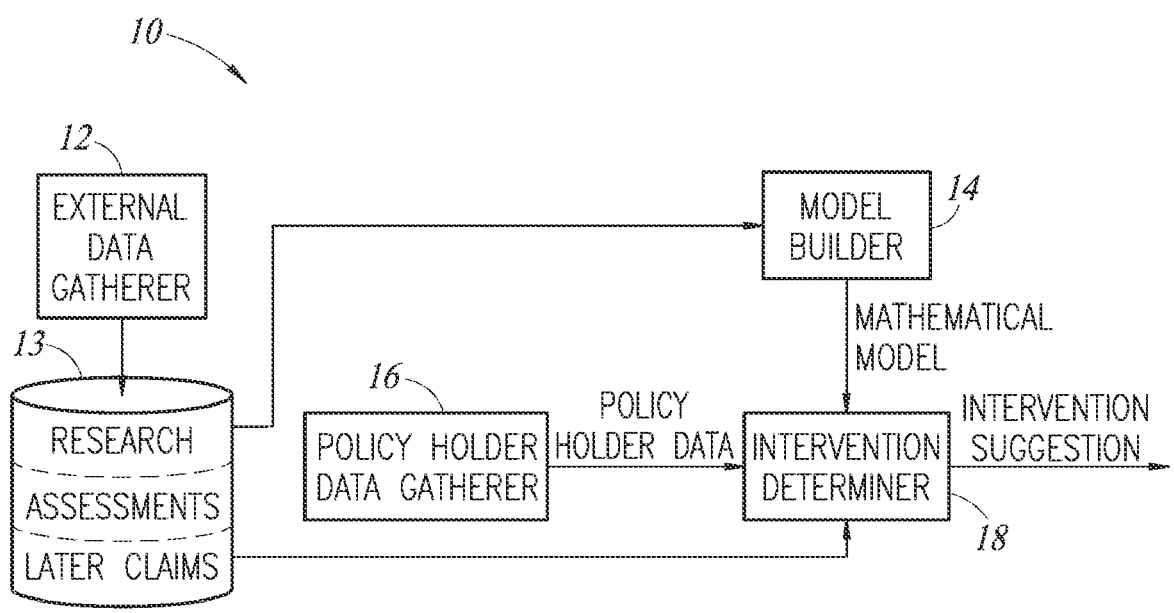
FIG. 1 is a schematic illustration of a population health management system, constructed and operative in accordance with a preferred embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Applicant has realized that postponing a claim for long term care is good for the policy holders as well as for the insurer. Moreover, Applicant has realized that, by gathering additional data about policy holders (i.e., other than that which insurance companies typically gather about their policy holders), it is possible to find those elderly policy holders who are more likely to activate their long-term care insurance policies in the near term and to provide them with suggestions to achieve a short-term improvement in their health and aging in place status. This may enable those elderly policyholders (i.e., those who are 80 years old and older), to age safely, healthily and independently.

Reference is now made to FIG. 1, which illustrates a health management system 10 for providing intervention suggestions to aid policy holders to not need long term care and/or to remain independent and/or at home, at least for a short term, such as 1 year.

Health management system 10 comprises an external data gatherer 12, a database 13, a model builder 14, a policy holder data gatherer 16 and an intervention determiner 18. External data gatherer 12 may gather data from multiple sources and may store the gathered data in database 13. For example, external data gatherer 12 may receive basic information about policy holders from the insurance company which issued the insurance policies. According to a preferred embodiment of the present invention, external data gatherer 12 may gather assessment data about the policy holders over a period of time, such as 6 months to a year. The assessment data may be the results of questionnaires sent to the policy holders, phone or home assessments made by social workers talking to or visiting the policy holders, observations by medical professionals, etc. At the same time, external data gatherer 12 may receive information about when the policy holders made a claim and for what type of care. External data gatherer 12 may also add research about health issues and, in particular, research about improving quality of life, etc. to the gathered data.

Using at least the assessment data and the claims data, model builder 14 may build a mathematical model, described in more detail hereinbelow, which may predict which candidates are more likely to make claims to long term care and within what time frame. Intervention determiner 18 may use the mathematical model to predict if a particular policy holder may benefit from an intervention, based on the results of recent assessments on that policy holder as gathered by policy holder data gatherer 16.

It will be appreciated that system 10 may provide improved risk management for the insurance company using it, based on improved data collection from policyholders, predictive modeling to target opportunities for intervention and deployment of science-based interventions. System 10 may reduce the likelihood of a claim in the near-term, since some claims will be deferred, while some will be shorter. Moreover, system 10 may monitor the interventions and their results and may update the model as a result.

Reference is now made to FIG. 2, which illustrates an exemplary questionnaire 30 which may be used for an assessment, and may be filled in by the policy holder, or by a social worker, nurse or physician, whether during a phone assessment or a home visit.

Each questionnaire 30 may have a plurality of questions 32, which may be categorized into multiple categories 34. For example, category 34a may be "living environment" while category 34b may be "home accessibility". Category 34a may have questions 32 like "Are you able to travel around the local area/community without problems?" and a question about "walkability" which may ask further questions about the quality of the external environment for walking (i.e., whether or not there are dedicated sidewalks and marked crossings for pedestrians, and shops, parks, and other destinations within walking distance, whether the climate is conducive to regular walking, etc.).

Category 34b may have questions about the feasibility of adjusting certain elements in the premises, about the convenience and presence of security peep holes for the particular policy holder.

FIG. 2 shows additional questions in categories such as financial sustainability, medical issues, life engagement, mental issues and functionality, all of which may affect a person's ability to handle problems when they are arrive, without having to register a claim against their insurance policy.

Reference is now made to FIG. 3, which illustrates an exemplary method of scoring questionnaire 30 which may be utilized by external data gatherer 12. Once external data gatherer 12 may finish scoring questionnaire 30, it may store the results in database 13.

As can be seen in FIG. 3, each Yes answer may be given a score of 1 while each No answer may be given a score of 0. Certain questions, like the question "How often do you feel that you lack companionship?" may give a score of 1 if the answer is above a certain number of times. Questions may be positive or negative and scoring may be the same for both or may be different. In the latter, scores to negative questions may be negative. In an alternative embodiment, questions may be kept "in the same direction". In a further alternative embodiment, questions may be either, so scores of questions that correlate to bad physical/cognitive/mental abilities will increase the global score.

As mentioned hereinabove, external data gatherer 12 may store the scores in database 13, along with any information about the policy holder that it may receive from the insurance company holding the policy. The insurance company typically provides basic contact information, some medical information, and information regarding when and which claims have been made.

External data gatherer 12 may provide assessments to all members of a group, such as a block of policy holders. Alternatively, external data gatherer 12 may reduce the size of the group to be assessed by any suitable method, such as by using a selectable set of different assessments.

Figure 4:
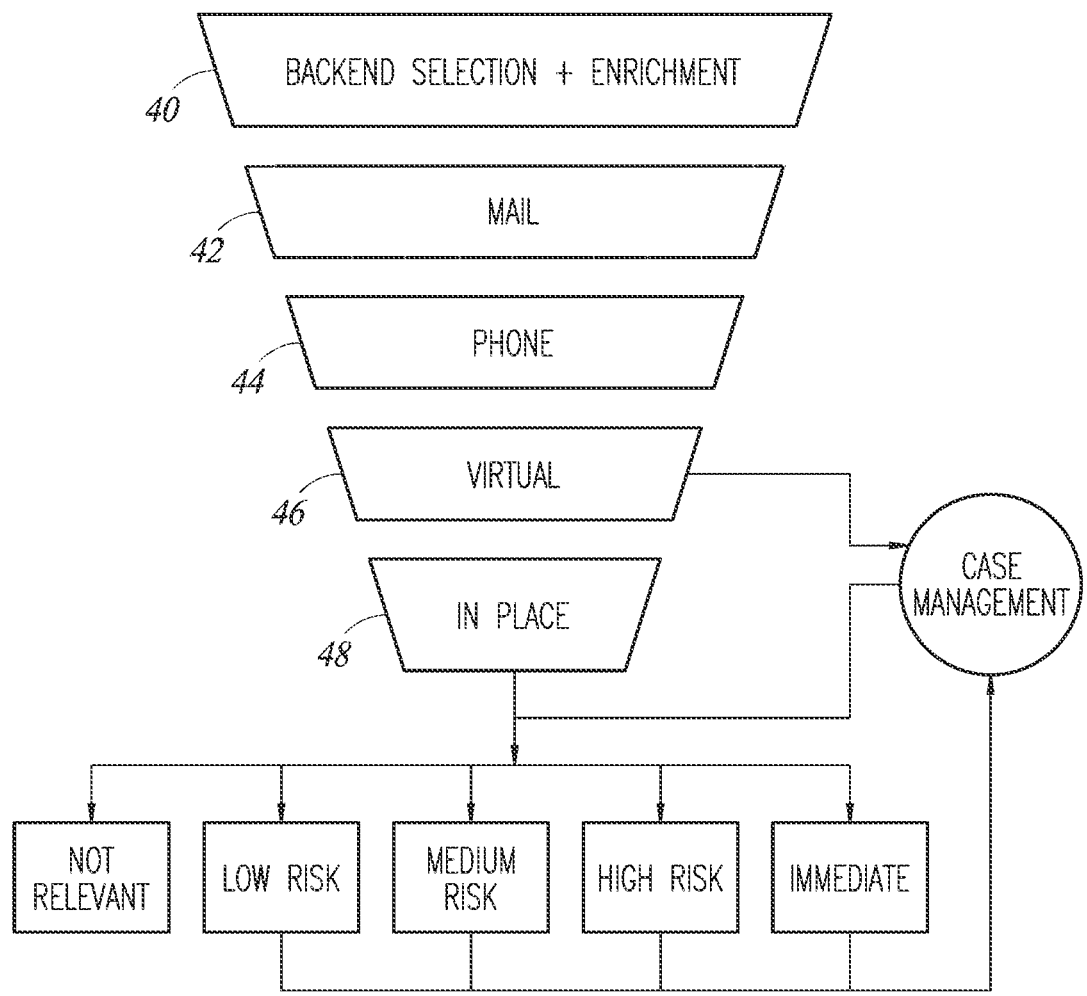
FIG. 4 is a schematic illustration of a method of selecting policy holders to receive different assessments.

For example, and as shown in FIG. 4 to which reference is now made, external data gatherer 12 may request (step 40) that a user initially define a sub-group of the group, after which external data gatherer 12 may mail (step 42) questionnaires to the members of the sub-group. Of these, external data gatherer 12 may request that a social worker or medical professional call (step 44) some of the "mailed to" members and of those "called to" members, external data gatherer 12 may request that a social worker or medical professional virtually assess (step 46) some of the called members. Finally, external data gatherer 12 may request that a social worker or medical professional may assess in place (step 48) some of the virtually assessed members.

After each type of assessment 40-48, external data gatherer 12 may score the answers according to a pre-defined scoring definition (which may be the scoring method described for FIG. 3 or some other scoring method). External data gatherer 12 may then select those members whose score is above a pre-defined threshold as initial candidates for the next group to be assessed.

To select the next group, external data gatherer 12 may review the current expected costs to assess each of the initial candidates and may select only those candidates whose cost is acceptable. It will be appreciated that the costs for an in-place assessment may be too high for those candidates that live "far away" from wherever the assessors are. It will also be appreciated that not all the costs are financial. External data gatherer 12 may also include into the cost calculation the risk of upsetting a policyholder, or stimulating a policy holder to ask for services even though it is unlikely that they will receive the intervention, etc. External data gatherer 12 may utilize predetermined cost curves to determine the cost at each level of assessment and these curves may change over time.

Figure 5:
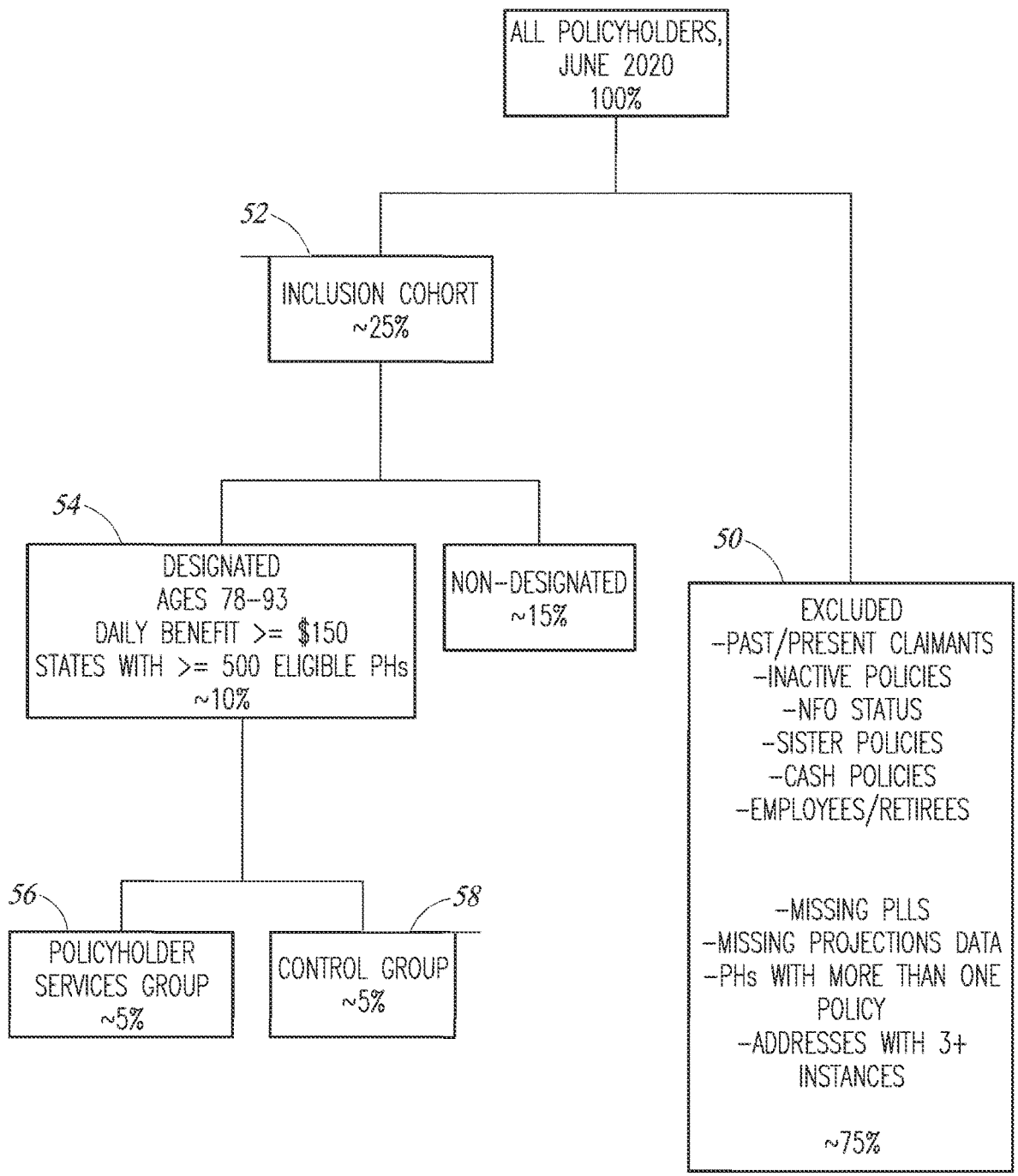
FIG. 5 is a schematic illustration of an example selection process to select policy holders for an initial data collection period.

External data gatherer 12 may collect the assessment data described hereinabove as well as claim data (when a claim was made and for what type of care) for a predetermined period of time, such as 6 months or 1 year, to provide sufficient data for model builder 14. FIG. 5, to which reference is now made, illustrates an example selection process to select policy holders for the initial data collection period. The initial selection may remove those policy holders 50 for whom intervention in the short term is unlikely to yield savings, or those who can otherwise not be engaged. The latter include those who have already made claims for long term care, whose policies are inactive, who are employees or retirees of the insurance company, they have more than one policy, more than one address is listed on the policy, etc.

Of the inclusion cohort 52, which in the example of FIG. 5 is 25% of the policy holders, only a portion may meet the intervention criteria, such as they are within the age range for interventions (ages 78-93), they have a daily benefit of over $150, and both policy holders of a joint policy meet the criteria. There may also be criteria related to a cost-benefit analysis determining what region is most beneficial to work in, such as its only cost-beneficial to provide interventions in a state having over 500 eligible policy holders. In FIG. 5, this designated portion 54 is only 10% of the block of policy holders. This may constitute the treatment pool.

For each of the policy holders of the treatment pool, external data gatherer 12 may obtain further information, such as contact information, from the insurance company or, if the insurance company does not have this information, from third party data sources, such as an online address service.

External data gatherer 12 may further define the treatment pool based on who can be contacted, and who among those is willing to engage with the program and may ask those willing to engage to provide information, e.g., by filling out a questionnaire. External data gatherer 12 may assign a score to all those who completed the questionnaire, and may continue the process, as described hereinabove with respect to FIG. 4, at a greater level of detail, for those whose score is above a threshold.

In one embodiment, assessment and claim data may be collected as described above for the treatment pool for the defined period of time. This may provide baseline data relating the assessment data to the claim and may be used to define risk levels (shown in FIG. 4), where those that are expected to file a claim within the next 1-2 years are high risk, within the next 2-3 years are medium risk, and within the next 3-5 years are low risk. Those that are expected to file a claim before the year is out are considered 'immediate'.

At a later point in time, the treatment pool may be divided in half (as shown in FIG. 5), into a pool 56 to receive interventions and a "control pool" 58 which does not receive interventions. Doing this may enable external data gatherer 12 to associate interventions and the resulting claims, which may enable intervention determiner 18 to generate an intervention table, discussed in more detail hereinbelow, for selecting those scientifically based interventions which may move claims to a later date.

It will be appreciated that the more detailed personal assessments may yield a stratification which may permit an individual treatment plan to be developed for the subset of policyholders whom intervention determiner 18 may determine offer the highest likelihood of a positive economic return relative to the cost of intervening.

Model builder 14 may generate a prediction model from the collected data (assessments and resulting claims) to determine the likelihood (i.e., expected risk level) that each policy holder in the treatment pool will file a claim for long term care within a predefined period of time.

Model builder 14 may utilize a predictive model of the type:

$$PC(\text{age}) = \frac{e^{(\Sigma \alpha_1 pet + \alpha_2 volunteer + \alpha_3 walks + ...)}}{1 + e^{(age^2 + \Sigma \alpha_1 pet + \alpha_2 volunteer + \alpha_3 walks + ...)}} \quad (1)$$

where PC(age) is the probability of filing a claim at age X and the features (pet, volunteer, walks, etc.) are the non-medical and medical scores provided through the assessments, most of which are generally not available to insurance companies. For example, some non-medical features might be: things an elderly person does, marital state, financial status, home ownership, social, smoker, etc., while some medical features might be those which can be measured at home, such as blood pressure, temperature, heart rate, etc. As mentioned hereinabove, each response on an assessment is scored and it is this score (1 or 0, per policy holder) which is used to define a value of a feature for model builder 14.

Model builder 14 may train on the data in database 13 to determine the impact coefficients $\alpha_i$ for each feature, where the initial values for impact coefficients $\alpha_i$ may be determined a priori from research data indicating the importance of one feature or another. During training, model builder 14 may change the values of impact coefficients $\alpha_i$ to match the data. It will be appreciated that, after training some impact coefficients $\alpha_i$ may be 0 or close to 0, indicating that those features are not likely to affect a claim for long term care.

Model builder 14 may perform a process similar to a logistic regression but one where one input is the age, another input is the square of the age, and some features, such as married and gender, may be co-dependent. Model builder 14 may select features automatically, beginning with age and one other feature and using them to attempt to match the data. Model builder 14 may then pick another feature and may check the extent to which the match to the data has improved. If it has improved, model builder 14 may keep the new feature. Otherwise, it may replace it with a different feature. Model builder 14 may continue the process until it has 4-5 features which, together, may provide the best match to the data in database 13. These features are, then, the ones which are most likely to affect whether or not a policy holder will make a claim at a given age.

In order to check the model, model builder 14 may initially divide the data in database 13 into two or more groups of policy holders and may use one group to determine the model and a second group to check that the model holds for them as well.

Model builder 14 may update the mathematical model over time, as external data gatherer 12 may collect more data and to reflect additional experience and knowledge in data gathering and in use of interventions, discussed in more detail hereinbelow. This may change which features may be included in the model.

Intervention determiner 18 may utilize the mathematical model generated by model builder 14 to define which interventions to suggest for a particular policy holder, once it has received the policy holder's scores from policy holder data gatherer 16.

Specifically, policy holder data gatherer 16 may determine what type of assessment(s) to make on a particular policy holder from among the questionnaire, phone, virtual and in-place assessment options and may score the results. This determination may be according to any suitable decision method, including the cost function method utilized by external data gatherer 12.

Intervention determiner 18 may utilize the mathematical model generated by model builder 14 on the scores received from policy holder data gatherer 16 to determine the risk level of the particular policy holder (i.e., the probability of a claim in the next year (i.e., when the policy holder is 1 year older)). If the risk level of the particular policy holder is high (i.e., above a predetermined level), intervention determiner 18 may rerun the model to see if a change in some feature will reduce the probability of this particular policy holder filing a claim. If so, intervention determiner 18 may suggest one or more interventions related to the changed feature to the particular policy holder. These interventions may be of the type which are designed to increase the likelihood of keeping that policy holder home for another year. Example interventions might be walking every day, some kind of home optimization, such as adding grab bars in the bathroom, engaging in social activities (e.g., religious services, clubs), improving medication administration and support, remote care coordination, managing loss of caregiver, preventing caregiver burnout, providing respite care and educating the policy holder about how to handle his/her diseases.

Intervention determiner 18 may utilize an intervention table 60, shown in FIG. 6 to which reference is now made, which may categorize possible interventions 62 according at least to the feature changes 64 determined by intervention determiner 18, since different interventions are known in the scientific literature as being appropriate for different feature changes. For example, if intervention determiner 18 determines that a change in the 'balance' feature may affect the probability of a claim from high risk to medium risk, then intervention determiner 18 may suggest a balance intervention, such as arranging for home modification. FIG. 6 shows multiple interventions per changed feature. These various interventions may have an order to them, such that the intervention may begin with the first intervention and, if a later assessment determines it necessary, further interventions may be added.

It will be appreciated that system 10 may be an adaptable system, which may be based on "machine learning". System 10 may start with an initial model based on research and expert opinions. However, as external data gatherer 12 may gather information from more and more policy holders, model builder 14 may update its models with "field data". Furthermore, intervention table 60 may be updated as the effectiveness of any of intervention may be determined (by research or by the number of claims after it has been used), or with new interventions.

Unless specifically stated otherwise, as apparent from the preceding discussions, it is appreciated that, throughout the specification, discussions utilizing terms such as "processing," "computing," "calculating," "determining," or the like, refer to the action and/or processes of a general purpose computer of any type, such as a client/server system, mobile computing devices, smart appliances, cloud computing units or similar electronic computing devices that manipulate and/or transform data within the computing system's registers and/or memories into other data within the computing system's memories, registers or other such information storage, transmission or display devices.

Embodiments of the present invention may include apparatus for performing the operations herein. This apparatus may be specially constructed for the desired purposes, or it may comprise a computing device or system typically having at least one processor and at least one memory, selectively activated or reconfigured by a computer program stored in the computer. The resultant apparatus when instructed by software may turn the general-purpose computer into inventive elements as discussed herein. The instructions may define the inventive device in operation with the computer platform for which it is desired. Such a computer program may be stored in a computer readable storage medium, such as, but not limited to, any type of disk, including optical disks, magnetic-optical disks, read-only memories (ROMs), volatile and non-volatile memories, random access memories (RAMs), electrically programmable read-only memories (EPROMs), electrically erasable and programmable read only memories (EEPROMs), magnetic or optical cards, Flash memory, disk-on-key or any other type of media suitable for storing electronic instructions and capable of being coupled to a computer system bus. The computer readable storage medium may also be implemented in cloud storage.

Some general-purpose computers may comprise at least one communication element to enable communication with a data network and/or a mobile communications network.

The processes and displays presented herein are not inherently related to any particular computer or other apparatus. Various general-purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the invention as described herein.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for selecting interventions for a particular policy holder of a long term care insurance policy, the method being implemented on a computing device, the method comprising:
   receiving claim data about when previous long term care insurance policy holders made a claim for long term care and for what type of care, for a block of policy holders, selecting a portion of said block which meets a set of intervention criteria;
   generating observation data over a period of at least 6 months about an ability of said portion of policy holders to handle problems when they are arrive, said observation data comprising medical data and self-sufficiency data about home environment, financial sustainability, life engagement, and functionality;
   using said computing device, providing scores to said at least said observation data and generating features as a function of said scores;
   generating scores based on said observation data
   using said computing device, building a probability based, predictive model from features based on a combination of said claim data and said observation data, at least two of said features being related to said self-sufficiency data, to identify which of said portion of policy holders are least likely to remain independent and/or at home during a next year;
   using said computing device, determining a reducible risk feature for an identified policy holder, identified by said model, from among said features, wherein said reducible risk feature is a changed feature of said model most likely to enable said identified policy holder to remain independent and/or at home during said next year;
   having an intervention table listing a set of interventions, each intervention having an associated reducible risk feature according to research data at least about improving quality of life, at least one of said interventions being non-medical, wherein said set of interventions comprises: a home optimization or modification, organizing transportation services, managing loss of a caregiver, preventing caregiver burnout, educating said particular senior about how to handle his/her diseases, encouraging said particular senior to engage in social activities, and encouraging said particular senior to be physically active; and
   using said computing device, identifying at least one intervention from said intervention table associated with said reducible risk feature for said identified policy holder to utilize as an aid to enable said identified policy holder to remain independent and/or at home for said next year, wherein said determining comprises:
   running said model with scores of said identified policy holder to generate a starting risk level of said identified policy holder;
   if said starting risk level indicates an expectation of said identified policy holder filing a claim within said one year of performing said building, changing one of said features included in said model to generate a changed model for said identified policy holder;
   running said changed model with said scores of said identified policy holder to generate a subsequent risk level for said identified policy holder;
   if said subsequent risk level is reduced from said starting risk level, selecting said changed feature as said reducible risk feature for said identified policy holder, otherwise repeating said changing and said running.

2. The method according to claim 1 wherein said building a model comprises generating impact coefficients for each said feature of said features.

3. The method according to claim 1 wherein said probability based, predictive model is based on at least one feature which is a function of age and at least a second feature which is a function of the square of said age.

4. The method according to claim 3 wherein said building a model comprises:
   calculating a match to said scores using said age feature and said square of said age feature;
   picking another feature;
   selecting said another feature if a match to said scores has improved; and
   repeating said calculating, picking and selecting until there are either no more features or no more improvement to said match.

5. The method according to claim 1 wherein said building a model comprising building an initial model from said research and updating said initial model with data from said policy holders.

6. A system for selecting interventions for a particular policy holder of a long term care insurance policy, the system implemented on a computing device, the system comprising:
   an external data gatherer to gather claim data about when previous long term care insurance policy holders made a claim for long term care and for what type of care, to select a portion of a block of policy holders which meets a set of intervention criteria, and observation data over a period of at least 6 months about an ability of said portion of policy holders to handle problems when they are arrive, said observation data comprising medical data and self-sufficiency data about home environment, financial sustainability, life engagement, and functionality;

a scorer to provide scores to said observation data and generating features as a function of said scores;

a model builder to build a probability based, predictive model from features based on a combination of said claim data and said observation data, at least two of said features being related to said self-sufficiency data, to identify which policy holders are least likely to remain independent and/or at home during a next year;

having an intervention table listing a set of interventions, each intervention having an associated reducible risk feature according to research data at least about improving quality of life, at least one of said interventions being non-medical, wherein said set of interventions comprises: a home optimization or modification, organizing transportation services, managing loss of a caregiver, preventing caregiver burnout, educating said particular senior about how to handle his/her diseases, encouraging said particular senior to engage in social activities, and encouraging said particular senior to be physically active; and an intervention determiner to determine a reducible risk feature for an identified policy holder, identified by said model, from among said features, wherein said reducible risk feature is a changed feature of said model most likely to enable said identified policy holder to remain independent and/or at home during said next year, and to identify at least one intervention from said intervention table associated with said reducible risk feature for said identified policy holder to utilize as an aid to enable said identified policy holder to remain independent and/or at home for said next year, said intervention determiner to: run said model with scores of said identified policy holder to generate a starting risk level of said identified policy holder;

if said starting risk level indicates an expectation of said identified policy holder filing a claim within said one year of performing said building, change one of said features included in said model to generate a changed model for said identified policy holder;

run said changed model with said scores of said identified policy holder to generate a subsequent risk level for said identified policy holder;

if said subsequent risk level is reduced from said starting risk level, select said changed feature as said reducible risk feature for said identified policy holder, otherwise repeat said changing and said running.

7. The system according to claim 6, said model builder to generate impact coefficients for each said feature of said features.

8. The system according to claim 6 wherein said probability based, predictive model is based on at least one feature which is a function of age and at least a second feature which is a function of the square of said age.

9. The system according to claim 8, said model builder to:
calculate a match to said scores using said age feature and said square of said age feature;
pick another feature;
select said another feature if a match to said scores has improved; and
repeat until there are either no more features or no more improvement to said match.

10. The system according to claim 6, said model builder to build an initial model from said research and updating said initial model with data from said policy holders.

* * * * *